(12) United States Patent
Nikolovski (10) Patent No.: US 12,076,279 B2
(45) Date of Patent: Sep. 3, 2024

(54) ULTRASONIC OBJECT DETECTION

(71) Applicant: COMMISSARIAT A L'ENERGIE ATOMIQUE ET AUX ENERGIES ALTERNATIVES, Paris (FR)

(72) Inventor: Jean-Pierre Nikolovski, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 672 days.

(21) Appl. No.: 17/258,949

(22) PCT Filed: Jul. 9, 2019

(86) PCT No.: PCT/FR2019/051702
§ 371 (c)(1),
(2) Date: Jan. 8, 2021

(87) PCT Pub. No.: WO2020/012110
PCT Pub. Date: Jan. 16, 2020

(65) Prior Publication Data
US 2021/0121331 A1      Apr. 29, 2021

(30) Foreign Application Priority Data

Jul. 10, 2018   (FR) ...................................... 1856357

(51) Int. Cl.
*A61F 9/08* (2006.01)
*A61F 9/00* (2006.01)
(Continued)

(52) U.S. Cl.
CPC ................. *A61F 9/08* (2013.01); *A61F 9/00* (2013.01); *G01S 7/521* (2013.01); *G01S 7/5208* (2013.01); *G01S 15/93* (2013.01)

(58) Field of Classification Search
CPC .......... G01S 15/00; G01S 15/02; G01S 15/04; G01S 15/87; G01S 15/88; G01S 15/93;
(Continued)

(56) References Cited

U.S. PATENT DOCUMENTS 5,107,467 A  * 4/1992 Jorgensen .............. A61H 3/061
                                                      367/99
6,198,395 B1    3/2001 Sussman
(Continued)

FOREIGN PATENT DOCUMENTS

CN          2500297 Y    7/2002
CN       105997448 A    10/2016
KR    10-2016-0081589 A  7/2016

OTHER PUBLICATIONS

NPL Search {Oct. 4, 2023).*
(Continued)

*Primary Examiner* — Van T Trieu
(74) *Attorney, Agent, or Firm* — Oblon, McClelland, Maier & Neustadt, L.L.P.

(57) ABSTRACT

A device for ultrasonic object detection, having at least two independent transducers that are able to emit at least two ultrasonic signals respectively in order to produce reflected ultrasonic signals in return, and able to receive the reflected ultrasonic signals, wherein it has an electronic processing unit configured so as to convert the received reflected ultrasonic signals into respective spectrograms, in an audible frequency band, and form respective audible temporal signals through an inverse Fourier transform of the spectrograms.

12 Claims, 4 Drawing Sheets

(51) Int. Cl.
*G01S 7/521* (2006.01)
*G01S 7/52* (2006.01)
*G01S 15/93* (2020.01)

(58) Field of Classification Search
CPC ... G01S 7/52; G01S 7/521; G01S 3/80; A61F 9/00; A61F 9/08; A61H 3/00; A61H 3/06; H04B 11/00; G10L 17/00; G01K 11/175; G06K 9/00
See application file for complete search history.

(56) References Cited

U.S. PATENT DOCUMENTS

| | | | |
|---|---|---|---|
| 9,508,269 B2 * | 11/2016 | Slamka | G01C 21/20 |
| 10,558,420 B2 * | 2/2020 | Osterhout | G06F 3/1454 |
| 10,591,728 B2 * | 3/2020 | Shams | G06F 3/0346 |
| 2010/0204991 A1 * | 8/2010 | Ramakrishnan | G10L 17/00 |
| | | | 382/118 |
| 2012/0062357 A1 | 3/2012 | Slamka | |

OTHER PUBLICATIONS

International Search Report issued on Nov. 4, 2019 in PCT/FR2019/051702 filed on Jul. 9, 2019, 2 pages.
French Preliminary Search Report issued on May 22, 2019 in French Application 1856357 filed on Jul. 10, 2018 (with English translation of Categories of Cited Documents), 2 pages.

* cited by examiner

ULTRASONIC OBJECT DETECTION

TECHNICAL FIELD

The present invention relates to the field of ultrasonic object detection, more specifically for the purpose of providing spatial information in stereo audio form. It applies to any context of impaired vision.

PRIOR ART

Equipping a pair of glasses with an ultrasonic sensor to assist the visually impaired in avoiding obstacles is known from the prior art. For example, document KR 20160081589 describes such a device, which also includes a loudspeaker to emit an alarm when the distance between the glasses and the obstacle drops to less than a predetermined value. The sound alarm is a beep and its repetition rate increases as the distance to the obstacle decreases. The sound alarm can be supplemented with vibrotactile feedback whose vibration frequency changes with the distance. The glasses incorporate a GPS to follow the path traveled. This type of device converts spatial information into sound or vibration information that is easy to interpret but relatively poor.

Document CN 2500297 describes glasses equipped with an ultrasound emitting transducer and two ultrasound receiving transducers. An electronic circuit makes audio signals from the signals received by the receivers. The audio signals are sent to earphones intended to be worn by a user. The processing performed on the signals received by the receivers does not alter the duration of the echo, so that it is the amplitude of the output signal that varies as a function of the more or less strong echoes caused by the surrounding objects. The result is not necessarily readily perceptible to the human brain and does not allow for a fine discernment of the surrounding objects. In addition, this device only includes a single emitting transducer, which limits the possibilities for distinguishing the contours of objects. Lastly, this emitting transducer has only one radiation diagram, which limits the space that can be probed.

Document U.S. Pat. No. 5,107,467 describes an echolocation system for a blind person, comprising means for emitting ultrasonic bursts toward objects, means for receiving the echo and generating an echo signal for each sound burst received with a certain real triggering delay caused by the propagation delay of sound waves in air, and means for adding an additional delay. The echo signal is typically composed of numerous signals reflected by objects located at various distances from the microphone, and signals that have bounced off various objects several times. The echo signal has an echo profile that is retrieved as an echo profile signal, which eliminates the burst frequency and makes the echo signal audible. The echo profile signal is applied to a variable delay circuit so as to add thereto a delay that increases with the distance of echogenic objects. The signal processing performed is therefore aimed at remaining within the time domain. In other words, the processing only accounts for the reaction time of the auditory system within the time domain. This processing is relatively basic, which does not allow for much wealth in the reproduction for the user.

There is a need to considerably improve the capacity of spatial perception in a context of impaired or impossible vision, or in the event that the visual cognitive load is already greatly solicited.

DISCLOSURE OF THE INVENTION

The invention is intended to solve the problems of the prior art by providing an ultrasonic object detection device including at least two independent transducers capable of emitting at least two ultrasonic signals, respectively, to produce as feedback reflected ultrasonic signals, and capable of receiving the reflected ultrasonic signals, characterized in that it includes an electronic processing unit configured to:

convert the reflected ultrasonic signals received into corresponding spectrograms, within an audible frequency band, and form corresponding audible time signals by inverse Fourier transform of the spectrograms.

The present invention makes it possible to enrich the user's perception of the environment. Indeed, it does not issue an alarm when a situation is detected as critical for the user as a function of the logical validation of a test criterion, but instead continually provides the user with signals representing his/her environment, which the user interprets as a function of his/her own experience, analogies, deductive reasoning, and so on. The present invention therefore provides the user with rich conditional information so that the user can perform his/her own mental analysis of the situation.

An alarm is stressful because it solicits immediate attention and requires an adapted response. Thanks to the invention, the reproduced signal can be listened to continually by the user and is not per se a stressful signal unless its interpretation leads to an alarming situation.

The present invention provides spatial information in the form of stereo audio in a context of impaired or impossible vision, or in the event that the difficult, impossible or in the event that the visual cognitive load is already greatly solicited.

Its purpose is to considerably improve the user's capacity for spatial perception nearby and/or at several meters.

In particular, it uses the capacity of the human brain to perform stereo time/frequency analysis in speech processing, that is, to understand words, so as to present sounds that are actually representative of the ambient echographic signal or acoustic signal in the ultrasound band.

The user builds a sound mental image of the environment based on the sounds the user hears.

According to a preferred feature, the electronic processing unit can be connected to an audio reproduction headset in order to reproduce the corresponding audible time signals. The audio signals are thus provided to the user.

According to a preferred feature, the electronic processing unit can furthermore be connected to an external device capable of performing at least a portion of the processing performed on the signals. Depending on the application, it may be advantageous to offload a portion of the processing.

According to a preferred feature, the ultrasonic object detection device further includes an accelerometer, a magnetometer, and a gyroscope for associating an orientation in relation to vertical and magnetic north with the probed solid angle. This additional information helps to enrich the information supplied to the user.

According to a preferred feature, the ultrasonic object detection device further includes a capacitive sensor or an accelerometer for activating the object detection device or putting it on standby. Thus, the object detection device is activated or put on standby by the user in a simple and intuitive way.

According to a preferred feature, the ultrasonic object detection device further includes a dual-frequency, triple-radiation-diagram, triaxial transducer. Such a transducer makes it possible to probe three regions of space in a simple way.

According to a preferred feature, the dual-frequency, triple-radiation-diagram, triaxial transducer includes:
- an annular metal resonator with central narrowing with a cylindrical shoulder,
- two annular-shaped piezoelectric ceramics arranged on either side of the metal resonator, one for causing a vibration of the cylindrical shoulder according to the axis of symmetry thereof, and the other for causing vibrations according to two axes that are mutually perpendicular and perpendicular to the axis of symmetry of the cylindrical shoulder.

The invention also relates to a pair of glasses equipped with an ultrasonic object detection device as presented hereinabove.

The invention also relates to a method for ultrasonic object detection including steps for:
- emitting at least two ultrasonic signals by at least two independent transducers, respectively, to produce reflected ultrasonic signals as feedback,
- receiving the reflected ultrasonic signals by the at least two independent transducers, characterized in that it includes steps for:
- converting the reflected ultrasonic signals into corresponding spectrograms, within an audible frequency band, and
- forming corresponding audible time signals by inverse Fourier transform of the spectrograms.

According to a preferred feature, the conversion of the reflected ultrasonic signals into corresponding spectrograms includes a projection of values of digitized signals formed from the reflected ultrasonic signals over at least a portion of the audible frequency band.

According to a preferred feature, the method of ultrasonic object detection further includes a step for amplifying the reflected ultrasonic signals received with a gain proportional to the delay. Thus, the ultrasonic signals reflected by more distant objects have an increased amplitude to attract more attention to those objects.

According to a preferred feature, the method of ultrasonic object detection further includes a step for translating the spectrograms.

The method has advantages comparable to those presented earlier.

In one particular embodiment, the steps of the method according to the invention are implemented by computer program instructions.

Consequently, the invention also relates to a computer program on a non-transitory information medium, said program being capable of being implemented in a computer, said program including instructions for implementing the steps of a method as described above.

The program can use any programming language and can be in the form of source code, object code, or code part way between source code and object code, such as in a partially compiled form, or in any other desirable form.

The invention also relates to a non-transitory information medium readable by a computer and including computer program instructions for implementing the steps of a method as described above.

The information medium can be any entity or device capable of storing the program. For example, the medium can include a means of storage, such as a ROM, for example a CD-ROM or a microelectronic circuit ROM, or a means of magnetic recording, for example a hard drive, or a flash memory such as a USB key.

Furthermore, the information medium can be a transmissible medium such as an electrical or optical signal, which can be sent over an electrical or optical cable, by radio, or by other means. In particular, the program according to the invention can be downloaded over a network such as the Internet.

Alternatively, the information medium can be an integrated circuit into which the program is incorporated, the circuit being designed to execute or to be used in the execution of the method according to the invention.

BRIEF DESCRIPTION OF THE FIGURES

Other features and advantages will become clear from a reading of the following description of a preferred embodiment, given as a non-limiting example, described in reference to the figures, in which.

DETAILED DESCRIPTION OF PARTICULAR EMBODIMENTS

The invention relates to an ultrasonic object detection device including at least two independent transducers capable of emitting at least two ultrasonic signals, respectively, to produce as feedback reflected ultrasonic signals, and capable of receiving the reflected ultrasonic signals. The device includes an electronic processing unit 3 configured to:
- convert the reflected ultrasonic signals received into corresponding spectrograms, within an audible frequency band, and
- form corresponding audible time signals by inverse Fourier transform of the spectrograms.

It should be noted that the frequency range of the ultrasound is, in practice, between 20 kHz and 200 kHz in air, and between 50 kHz and 5 MHz in a liquid medium. The audio reproduction range is between 20 Hz and 20,000 Hz, and preferably between 100 Hz and 8000 Hz.

Figure 1:
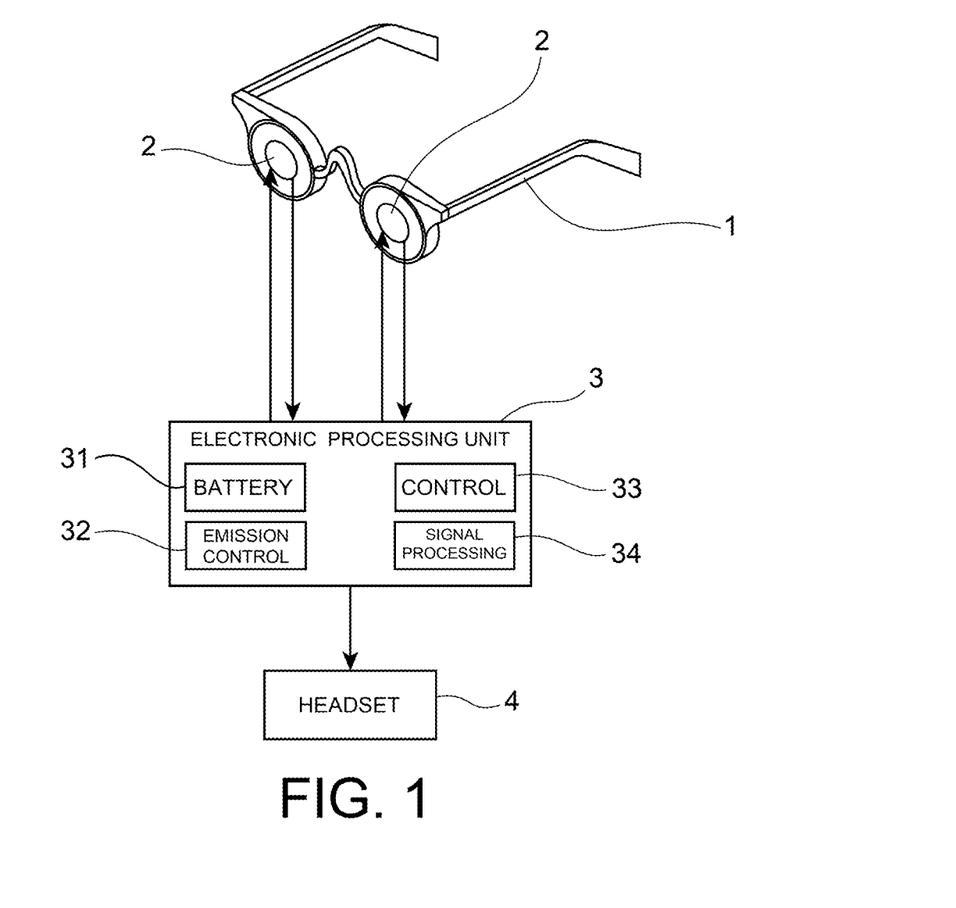
FIG. 1 shows an ultrasonic object detection device according to one embodiment of the invention.

According to a preferred embodiment shown in FIG. 1, the ultrasonic object detection device is arranged on a substrate 1 in the form of a pair of glasses to be worn by a user. These glasses are more specifically intended to be used in a fluid medium—air or water—if the user's vision needs to be improved either because the user is blind or because the medium does not allow for adequate vision. The term echovision is used when referring to the perception of the contours of objects and the boundaries of the surrounding space, and echo-stereo-sound when referring to the inspection of the insides of objects, as in the marine environment.

As a variant, the device equips a vehicle or a motorcycle helmet to provide echovision in a direction not visible to the driver. According to another variant, the device equips a diving mask. The device can further equip a handle intended to be held by a hand.

The ultrasonic object detection device includes the two ultrasound transducers arranged on the pair of glasses. For example, the transducers are arranged in front of the user's eyes when the user is wearing the glasses. The transducers 2 are independent of each other and have center frequencies the value of which depends on the intended use. The center frequency is, for example, 40 kHz for distant echovision or 175 kHz for nearby echovision.

The number of transducers can be greater than two.

For a given propagation medium, the choice of ultrasound frequency is a compromise between detection distance and spatial resolution. For a good detection of the edges of objects or small irregularities in underwater echo-stereosound, it is advisable to work with high frequencies. Indeed, the beams of ultrasonic signal emitted at high frequencies are directional and allow for good detection of the contours of objects. In air, high frequencies are damped very quickly and their range is shorter. For example, at 175 kHz the range is a few tens of centimeters, whereas at 23 kHz, the range may reach as far as several tens of meters. Different pairs of glasses can be provided, some of which for short distances and providing good angular resolution, while others for long distances, and still others for an underwater environment.

The transducers 2 are configured to switch from an emission mode to a reception mode. For very short distance echovision, for example a few centimeters, the two transducers can be coupled together and synchronized so that one functions for emission while the other functions for reception.

The transducers 2 can be associated with parabolic antennas, not shown in FIG. 1. In this case, the vibrating surfaces of the transducers 2 are arranged in the focal plane of the antenna. The transducers 2 are sized to produce ultrasound in relatively well collimated beams, with an aperture angle of 7 degrees at 175 kHz.

The ultrasonic object detection device includes the electronic processing unit 3 connected to the transducers 2. The electronic processing unit 3 includes a battery 31, an ultrasound emission control module 32 for each transducer, a control module 33 for switching between the emission mode and the reception mode of each transducer, and a signal processing module 34 to perform the processing described hereinbelow.

The electronic processing unit 3 is connected to a sound reproduction headset 4 to be worn by the user.

In the event that headset also serves a passive and/or active noise-suppression function, it also preferably includes binaural microphones to capture the outside sound and reproduce it internally.

As a variant, the electronic processing unit 3 is furthermore capable of being connected to an external device capable of performing all or a portion of the processing performed on the signals. For example, this device is a smartphone, tablet, or computer.

As a variant, the ultrasonic object detection device also includes an accelerometer, a magnetometer, and a gyroscope arranged on the pair of glasses. This makes it possible, for example, to associate an orientation in relation to vertical and magnetic north with a probed solid angle and therefore to build a graphic audio representation of the environment as a function of the solid angle probed.

The device can additionally include a capacitive sensor or an accelerometer arranged on the pair of glasses, to allow the object detection device to be activated or put on standby, as explained hereinafter.

An embodiment of operation of the ultrasonic object detection device is described in the form of a method including steps for:

emitting at least two ultrasonic signals by at least two independent transducers, respectively, to produce reflected ultrasonic signals as feedback, receiving the reflected ultrasonic signals by the at least two independent transducers, converting the reflected ultrasonic signals into corresponding spectrograms, within an audible frequency band, and forming corresponding audible time signals by inverse Fourier transform of the spectrograms.

Figure 2:
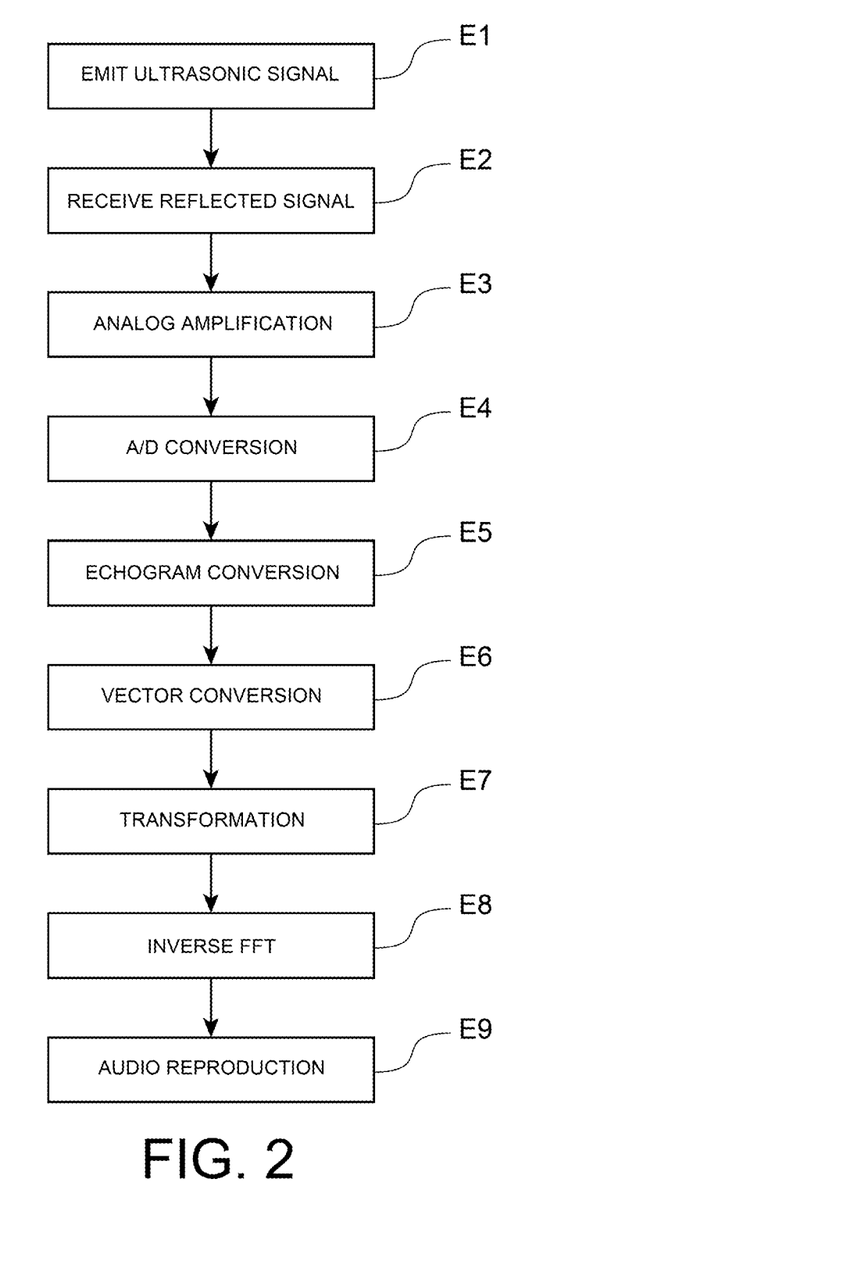
FIG. 2 shows an ultrasonic object detection method according to one embodiment of the invention.

FIG. 2 shows in greater detail an embodiment of operation of the ultrasonic object detection device in the form of a flowchart including steps E1 to E9.

The processing of steps E1 to E8 is described for a given transducer to simplify the description, but they are performed in parallel for both transducers.

Figure 3:
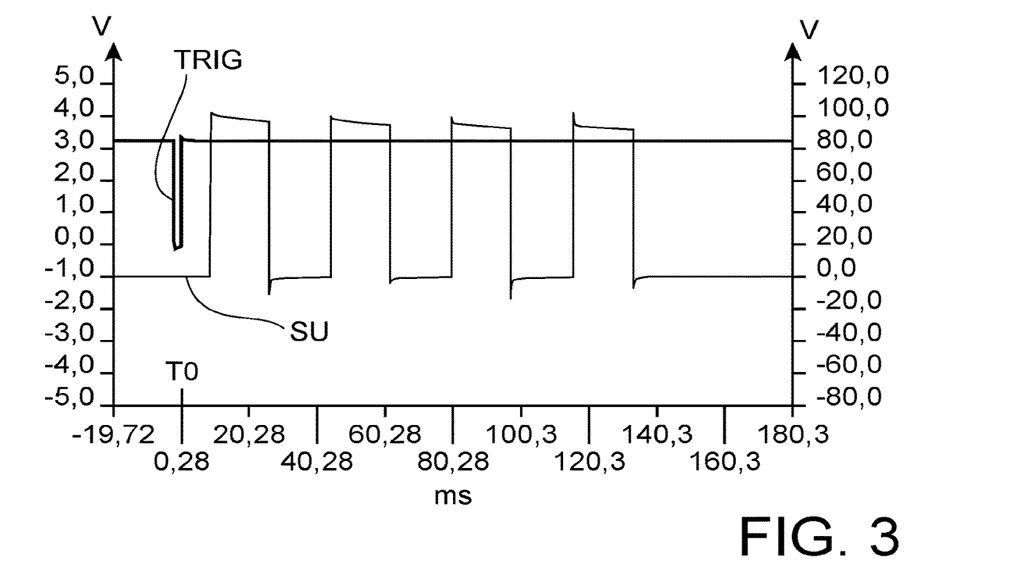
FIG. 3 shows an example of an ultrasonic signal emitted in one embodiment of the invention.

In step E1; the transducer 2 emits an ultrasonic signal. FIG. 3 shows an example of an ultrasonic signal SU. The transducer is in the emission mode and the emission is triggered by a synchronization signal TRIG coming from the electronic processing unit 3 itself if it is capable of emitting its own synchronization signal, or from an external device. Emission of the ultrasonic signal starts at instant TO with a rising edge of the synchronization signal. It must be noted that a fixed latency time may be included between the rising edge and the actual shot.

The period of the ultrasonic signal is adjustable and is preferably between 1 ms and 100 ms. Hereinafter, the period is considered to be 50 ms. The ultrasonic signal includes a number N of square pulses over one period, N typically being between 1 and 4, at a voltage of between 1 and 100 V, at the resonant center frequency of the transducer in question.

The width of a pulse is configurable and corresponds to the half-period of the resonant frequency of the transducer.

Preferably, the emission of ultrasound starts with a low amplitude of the excitation voltage. For example, amplitude of the excitation voltage can be a few volts at the beginning. This amplitude can then be increased automatically or by the user, for example, up to 100 V when the echo amplitude is low.

Figure 4:
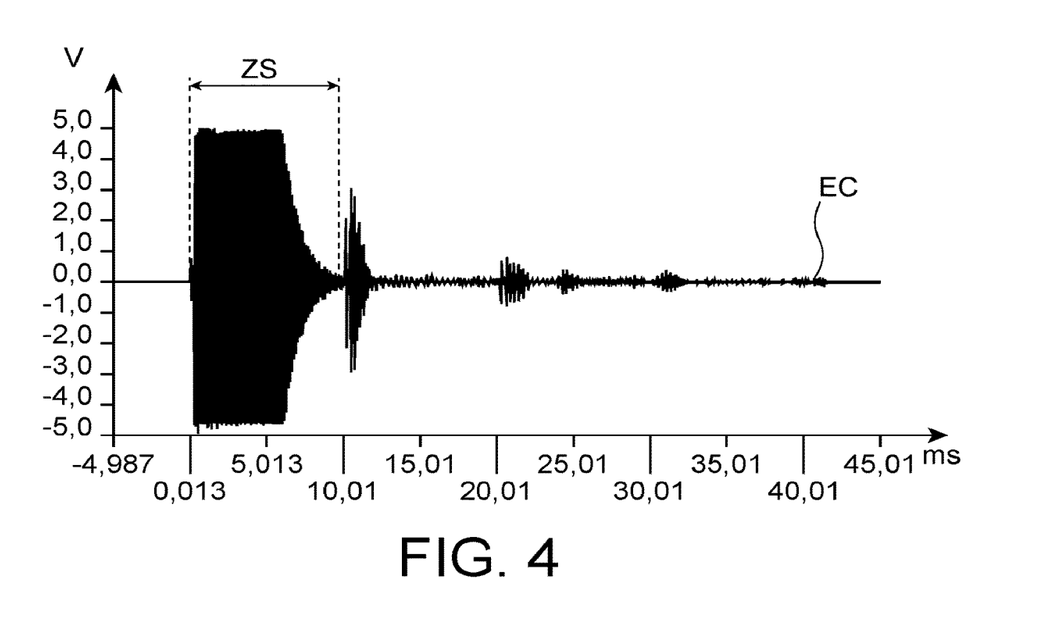
FIG. 4 shows an example of a sonogram received by a transducer in one embodiment of the invention.

The next step E2 is the reception of a reflected ultrasonic signal, or echogram, by the transducer. The transducer is switched to reception mode for this purpose. FIG. 4 shows an example of an echogram EC received by a given transducer. A 50-ms window is taken into consideration, which allows the space to a depth of 8.5 meters to be explored for an ultrasound propagation speed in air of 340 m/s and 5 times more in water.

First of all, the echogram EC includes a deaf zone ZS corresponding to the emission of the ultrasonic signal SU. Detection is not possible during this time interval.

The echogram EC then includes one or more peaks, each of which corresponding to an object or successive echoes from the same object. The position in time of each peak corresponds to the distance between the object and the transducer 2 that transmitted the ultrasonic signal.

By counting the travel time of a round trip of ultrasound in air, an object located 5 cm away thus produces a first peak after 0.3 ms, whereas an object located 17 cm away produces a peak after 1 ms. In emission/reception mode with just one transducer, the response pulse of the transducer must therefore be as short as possible, preferably less than ten acoustic periods of the transducer being used, so that nearby objects can be detected.

The next step E3 is an optional step for analog amplification of the echogram EC. The wave packets corresponding to the most distant echogenic objects arrive at the end of the echogram. They have a weaker intensity. A gain proportional to the delay can be applied to them to raise the amplitude of the ultrasonic signal of the most distant objects when special attention is to be focused on moving objects coming from afar. It is also possible to apply limited amplification to a portion of the echogram after a certain time or a given peak of the echogram. The gain is then increased proportionally to the time or according to an increasing monotonic law after the specific instant or the predetermined peak. The gain can be user-adjustable. The result is an amplified echogram.

The next step E4 is an analog-to-digital conversion of the amplified echogram. The echogram is sampled, for example, at a frequency of 164 kech/s to 12 to 15 quantization bits for an emission/reception center frequency of the transducer of 40 kHz. The result is a digitized echogram.

The next step E5 is a conversion of the digitized echogram to a digital signal of positive values. For example, the absolute value of each sample of the signal is used to make a positive digital signal.

Alternatively, steps E4 and E5 can be replaced with steps E4' and E5'. Thus, step E4' is a peak or profile detection of the analog echogram based on the absolute value of the analog signal. Then step E5' is an analog-to-digital conversion of the positive analog signal. In this case, the signal is sampled at a much lower sampling frequency, for example 44,100 Hz.

In both cases, the result of step E5 or E5' is a vector of positive values, generated from the profile of the echogram.

The next step E6 is a conversion of the vector obtained in the preceding step to a spectrogram. The vector built from the echogram is projected onto a spectrum occupying at least a portion of the audible band.

To do this, a homothety is applied to the vector built from the echogram. The homothety is an association between distance determined by the echogram and frequency. The association can be linear, for example the 0 Hz frequency component is associated with an echogenic object located at 0 centimeter, the 300 Hz frequency component is associated with an echogenic object located at 30 cm, and the 8000 Hz frequency component is associated with an echogenic object located at 800 cm. In this case, a homothetic association factor is 10 Hz/cm. If the round-trip travel speed in air of 17 cm/ms is factored in, then the echogram conversion coefficient is 170 Hz/ms.

In water, the distances are multiplied by 5 and in solids they are multiplied by a factor of between 2 and 4 compared to water, depending on whether transverse waves, longitudinal waves, or guided waves are being used. The conversion coefficient therefore depends on the propagation speed of the ultrasound in the chosen propagation medium.

The conversion coefficient also depends on the bandwidth of the chosen reproduction frequency. Indeed, the spectrum over which the vector is projected depends on the audio reproduction desired by the user. The projection spectrum can occupy the entire audible band. If the user wishes to continue to be able to listen to the ambient noise, particularly when traveling on a street, it is possible to contract the echogram so that it only occupies a band of 500 to 2000 Hz, and to translate it so that the distance of 0 centimeter starts at a frequency that is pleasant to the user, corresponding, for example, to the beginning of the emission spectrum of a bird, such as a nightingale. The bandwidth and the centering of the audio reproduction frequency band are preferably adjustable settings.

In practice, the conversion coefficient may be double or half or less, or possibly vary according to a logarithmic law (quick variation at close distances and slow at far distances) depending on the usage preferences and bearing in mind a possible presbycusis or auditory deficiency of the user.

All of steps E4 to E6 are thus a conversion of the received reflected ultrasonic signal into a spectrogram in an audible frequency band.

The next step E7 is a transformation of the spectrogram in order to give it the mathematical characteristics of a modulus-based digital spectrum obtained by Fast Fourier Transform, FFT. To do this, the spectrogram is periodized at an audio reproduction sampling frequency. The result is a phase-equivalent spectrogram.

For example, the spectrogram typically occupying the band from 0 to 8000 Hz is considered. An audio reproduction sampling frequency of 44,100 Hz is considered accessible to a smartphone or microcontroller. This assumes the availability of 2205 frequency components spaced 20 Hz apart to reproduce an audio signal over 50 ms.

Four hundred frequency components are enough to cover the spectrum from 0 to 8000 Hz. Knowing that 8192 time samples are available for a sampling of 163 kech/s, it is possible to perform a peak detection of this digital signal, and then a sub-sampling of 1 for 20 so as to only keep 400 representative samples of the spectrum from 0 to 8000 Hz.

The next step E8 is an inverse fast Fourier transform of the spectrogram obtained in the preceding step. The result is a time signal in the audible band. This signal is normalized to the amplitude of 1, which is the maximum amplitude level of an audio signal.

As a variant, an additional audio filter is added to the audio signal for listening comfort, so as to add harmonics to change the timbre of the reproduction. In this case it is a matter of sound colorization consisting in enriching the spectrum for the user's auditory comfort by adding a psychoacoustic effect.

As already mentioned, the processing of steps E1 to E8 are performed in parallel for both transducers. The result of step E8 is therefore two audio signals.

The next step E9 is the reproduction of the audio signals in the sound reproduction headset 4 intended to be worn by the user. The audio signal generated from the echogram emanating from the left transducer is sent to the left earphone, and the audio signal generated from the echogram emanating from the right transducer is sent to the right earphone.

The processed signal is reproduced continuously in juxtaposed 50-ms sections so that the user has the impression of scanning the space continuously and that there is continuity in the time sections. The ultrasound echoes therefore make it possible to "see" the environment in the form of sounds.

It is possible to emit an ultrasonic signal by one of the transducers every 50 ms in alternation, for example the right transducer then the other transducer, for example the left transducer. Thus, the audio signal generated for each ear is refreshed every 100 ms and a right or left audio signal is sent twice to the right or left earphone, respectively.

The user can then adjust the reproduction volume in the stereo earphones. Simultaneously listening to these two signals with movement of the head allows the brain to perceive the depth and profile of the relief, and therefore to form a sound image of the environment. If the left ultrasonic signal beam is reflected off the edge of an object and the right ultrasonic signal beam is already beyond the edge of the object, the reproduction signals will be different, producing different reproduction sounds that are perceptible to the auditory system and the human brain.

Indeed, thanks to the two independent reproduction channels, the two audio signals can be compared to each other by the user's auditory system. This comparison of two audio signals allows for a finer frequency analysis by the brain than if only one audio signal were produced. For example, it is easier to determine that the right audio signal has a higher frequency than the left audio signal, and therefore to deduce that the obstacle is a little further away on the right than on the left, than it is to determine a distance based on a frequency of a single audio signal. In particular, the angular and axial resolutions are obtained by the systematic comparison of the right and left reproductions.

This must make it possible to distinguish, for example, a plate, utensils, the fill status of a glass, a doorknob, the edge of a sidewalk, and the presence of a post. With a coefficient of 10 Hz/cm, a glass filled with 1 cm of water held at 40 cm from the ultrasound transducers produces a sound reproduction with a 400 Hz component compared to the same glass, but empty, held at the same distance, which produces a sound reproduction with a 410 Hz component. Unless one is endowed with perfect pitch, it is difficult to differentiate between a sound at 400 Hz versus 410 Hz. However, with stereo hearing it is very easy to hold a glass in one's hands, make the water swirl in the bottom of the glass, and produce a frequency modulation between 400 Hz and 420 Hz corresponding to an echo on the surface of the moving liquid which can move by +/−2 cm from its position of equilibrium. The stereo time-frequency analysis allows the brain to finely perceive this beat frequency of 0-20 Hz around 400 Hz. In addition, for an even finer perception of nearby objects, the coefficient could be greater for nearby objects, for example up to 20 Hz/cm, and be less for more distant objects.

In an underwater environment, for example in exploration, with echo-stereo-sound, stereo reproduction can allow anomalies such as breaks in acoustic impedance to be detected and assessed.

If the device includes an accelerometer, a magnetometer, and a gyroscope, it is possible to associate an orientation in relation to vertical and magnetic north with the probed solid angle and therefore to build a graphic representation of the type angular C-scan of space, that is, a stereo tomography of the environment as a function of the probed solid angle.

The combination of the accelerometer and the magnetometer makes it possible to define the attitude and azimuth of the inspected direction with the aim of recording the properties of the probed space, particularly with echo-stereo-sound. In this case, the reproduction is both audio for the real-time portion (50-ms sections) and graphic for the graphic reconstitution and recording of the azimuthal scan in polar coordinates. The iso-level echoes are shown in colors or shades of grey. When the glasses are used for blind orientation, the azimuth indication is reproduced by superimposing intelligible words (North, North-East, East, South-East, South, South-West, West, North-West) or by an angle giving the azimuth, while the longitudinal attitude can also be simply described by intelligible words superimposed on the audio reproduction (up, horizontal, down) or by an angle in degrees declared when threshold values are crossed (−90°, −45°, −45°, 0, 45°, 90°) with 10 to 20 degrees of hysteresis.

Steps E1 to E8 are performed by the electronic processing unit 3. As a variant, the electronic processing unit 3 is furthermore connected to an external device capable of performing all or a portion of the processing performed on the signals. For example, this device is a smartphone, tablet, or computer.

In this case, steps E4' and E5' are preferably implemented. Step E4' is a peak or profile detection of the analog echogram based on the absolute value of the analog signal.

Next, the profile of the analog echogram is sent to the external device, such as a smartphone, via the audio/microphone jack connector thereof. The following steps are performed by the smartphone. In particular, step E5' for analog-to-digital conversion of the positive analog signal is performed with a lower sampling frequency, for example 44,100 Hz, than when the processing is performed in the electronic processing unit 3.

According to another variant, the method also includes emission of the echograms or spectrograms to a remote device, such as a server associated with a database storing echograms or spectrograms. This device compares the echograms or spectrograms to those of the database. Such information, such as the spoken language generated by voice synthesis, is built from comparison results and is then reproduced for the user. This variant helps the user to learn.

The object detection device is activated or put on standby via a capacitive sensor or an accelerometer arranged on substrate 1 and connected to the electronic processing unit 3.

The accelerometer is placed on the transducer holding plate and indicates if the user is at rest, for example if the user is lying down or not moving. In addition, various commands can be issued by the user by means of the accelerometer. For example, increasing the audio reproduction or the intensity of the emissions can be triggered by small jerky up and down nods of the head to say "yes more," whereas a reduction in the intensity of the emissions and, ultimately, putting the device on total standby after 5 or 6 jerky shakes, is obtained by jerky right-to-left movements detected by the accelerometer to say (no=lower=stop after 5 to 6 alternating shakes).

In this way it is possible to keep the glasses in standby mode and activate them simply by nodding one's head. Electrical power consumption is low.

The capacitive sensor allows for projected-field capacitive detection of the opening (=activation) or closing (=stopping) of the user's eyelids. The capacitor placed on the rear portion of the plates holding the transducers has electrostatic field lines going up to the eye located at less than 2 cm, so that movement of the eyelid generates a variation in the capacitor's capacitance that can be quantified via a capacitor bridge or via a relaxation oscillator with an oscillation frequency that is directly dependent on the capacitance of the capacitor.

Of course, it is possible to program the opposite situation, in particular for sighted persons using the device for rear vision, that is, to stop the ultrasonic signal emissions when the eyes are closed, and to activate the emissions when the eyes are opened. In this case, the device is in operation much more often and it is preferable to replace the earphones with a headset that also provides a small amount of hearing protection of 20 to 30 dB.

In all cases, it is convenient to have both an accelerometer and a projected-field capacitive sensor to activate or deactivate the emissions and put on standby/wake up by opening/closing the eyelids and/or alternating up/down nodding and right/left shaking of the head.

It is worth noting that the command to stop or start the emissions is very simple for the user.

In addition, it may be attractive to have multifrequency transducers and a plurality of radiation diagrams, at least three, corresponding to three probed regions of space, one central and two peripheral, without having to build sophisticated electronics managing a network of phases to orient the ultrasonic signal beam according to laws governing delays between sources.

According to a particular embodiment, the glasses include for each eye a transducer that is both source and receiver at a given frequency, for example 23 kHz, providing peripheral vision, and a source/receiver transducer at another given frequency, for example 32.5 kHz or more, providing central vision.

The echograms associated with each of these transducers are converted into spectrograms, not superimposed, but translated with respect to each other. For example, the transducer with a center frequency 32.5 kHz used for central vision will occupy the 0-4000 Hz band, whereas the transducer with a center frequency of 23 kHz, used for peripheral vision, will occupy the 4000-8000 Hz band.

In the event that a contraction/translation of the spectrum is applied, the first echogram associated with the 32.5 kHz source will occupy the 3000-4000 Hz band, whereas the second echogram associated with the 23 kHz source will occupy the 4000-5000 Hz band, for example. Of course, this distribution is adapted and fine-tuned according to the user's preferences. Thus, by turning the head, the peripheral landscape gradually comes into the field and the audio reproduction gradually transitions from one frequency band to the other. In a certain way, the brain is given the possibility of achieving a mental focus by means of the dual-frequency echovision device.

Figure 5:
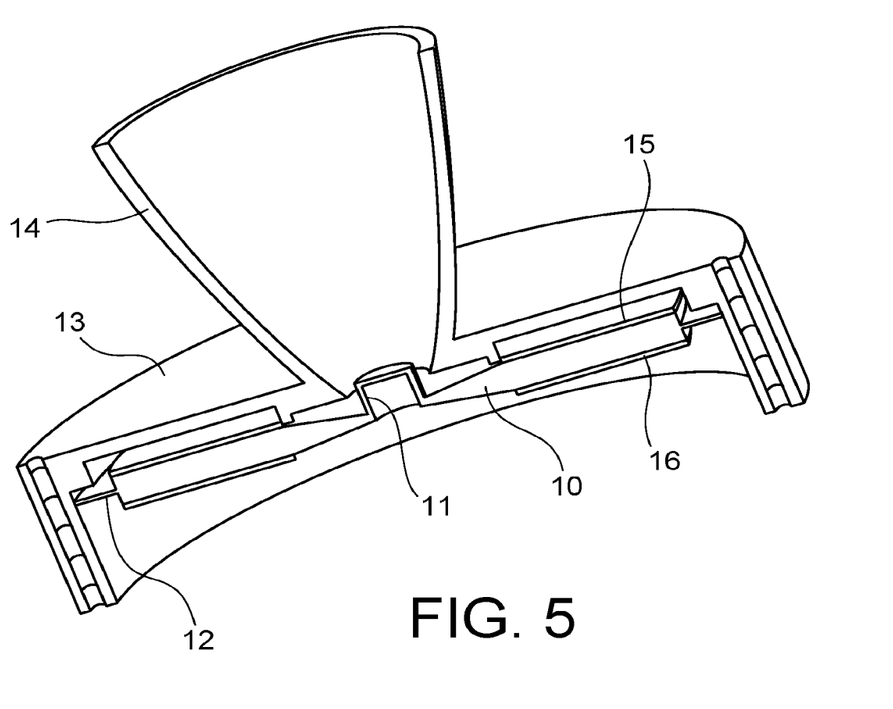
FIG. 5 shows a transducer with dual working frequencies according to one embodiment of the present invention.

FIG. 5 shows a cross-sectional view of one embodiment of a transducer with two working frequencies according to the present invention. The transducer is triaxial with two frequencies, for example F1=32.5 kHz and F2=23 kHz, and a triple radiation diagram.

The transducer consists of an annular metal resonator 10 made, for example, of Duralumin with a narrower central area. The annular resonator 10 includes a hollow cylindrical shoulder or sleeve 11 at the center thereof. The annular resonator also has on the perimeter thereof a thin collar for holding the annular resonator by clamping between a holder 13 comprising a parabolic antenna 14 and a closing flange not shown.

The transducer is thus incorporated into the holder thereof with the parabolic antenna 14.

The outer surface of the cylindrical shoulder is located in the focal plane of the parabolic antenna. The thickness of the metal resonator 10 is adjusted to define the desired center resonant frequency. The thicker the resonator 10 is along the perimeter thereof, the higher the resonant frequency. It increases in proportion to the square root of the thickness of the resonator.

Two piezoelectric ceramics 15 and 16 with an annular shape are bonded on either side of the metal resonator. The typical dimensions thereof are outside diameter 50 mm, inside diameter 20 mm, and thickness 0.5 mm.

The central cylindrical shoulder 11 can vibrate either by tilting or by moving up and down along the extension of the axis of symmetry thereof. In this case the resonance is called "out of plane" or "axial." Axial resonance at the harmonic frequency of 32.5 kHz is generated by the uniformly polarized upper piezoelectric ring 15.

The tilting resonance is generated by the lower piezoelectric ring 16, according to an axis perpendicular to the axis of symmetry of the cylindrical shoulder 11. In order to tilt the central cylinder 11, the outer electrode of the lower piezoelectric ring 16 is divided into two electrodes in the form of half rings. One of these two half-ring electrodes is excited with a positive voltage, such as 100 V, whereas the other is excited with a negative voltage, for example −100 V. The electrode on the rear surface remains uniform and constitutes ground. The two piezoelectric ceramics are polarized uniformly according to the thickness thereof. This tilting resonance occurs at a frequency F2=23 kHz, less than the axial resonant harmonic frequency F1.

The tilting can be controlled selectively according to two axes that are mutually perpendicular and perpendicular to the axis of symmetry of the cylindrical shoulder 11, by dividing the outer electrode of the lower piezoelectric ring 16 into four quadrants operating by opposing pairs at the top. In one pair, one of the electrodes is raised to a positive potential whereas the other electrode is raised to a negative potential. The tilting of the cylindrical shoulder 11 generates an acoustic wave, the radiation diagram of which is a FIG. 8 and is similar to a vibrating dipole. The intensity of the radiation is maximum along one axis for one dipole and along the perpendicular axis for the other dipole, and zero in the respective perpendicular directions.

Therefore, a single transducer having two independent ultrasound sources in elastic regime, which can also be driven at harmonic frequencies, particularly for axial resonance, is obtained.

Each transducer according to FIG. 5 is equivalent to a group of three transducers, one emitting forward at a frequency F1, according to a first horizontal radiation diagram perpendicular to the axis defined by the ears, the second at a frequency F2 laterally and horizontally to the left for the left ear and to the right for the right ear, that is, according to a radiation diagram of which the main axis is perpendicular to the preceding one, and lastly the third, also at the frequency F2, vertically up and down, that is, according to a radiation diagram of which the main axis is perpendicular to the preceding two.

The last two transducers of the group of three transducers are responsible for providing a mental peripheral sound image. These six transducers—three on the right and three on the left—can be excited sequentially and share a portion of the audio spectrum for reproduction. The third spectrum corresponding to the up-down radiation diagram is juxtaposed after the second spectrum corresponding to lateral vision, which is juxtaposed after the first spectrum corresponding to central vision. With regard to lateral echovision, there is a distinction between the spectrum of the left echogram which is juxtaposed to the spectrum of the right echogram.

In order for the ultrasonic signal emitted laterally to the left at the frequency F2 by the left transducer not to go to the right, the central parabolic antenna has no holes to the right, but only to the left. In a complementary way, in order for the ultrasonic signal emitted laterally to the right at the frequency F2 by the right transducer not to go to the left, the central parabolic antenna of the right transducer has no holes to the left, but only to the right.

Note that for a transducer according to FIG. 5, there is only one parabolic antenna 14 for the two vibration modes. However, it is possible to provide a second concentric parabolic antenna on the outside of the first to which the 23 kHz wave is sent by lateral emission, whereas the central antenna is reserved for axial emission at 32.5 kHz. To do this, small openings are made at the base of the central antenna adjacent to the end portion of the sleeve so as to allow the 23 kHz wave to reach the outer antenna. The outer antenna is much more open than the inner antenna, and even absent or flat with a hemispherical beam width of $2\pi$ steradians, and is responsible for probing the perimeter, whereas the central antenna is narrow and responsible for probing the axial field. A solution for peripheral echovision according to a tilting axis and a solution for central echovision are thus obtained.

The invention claimed is:

1. An ultrasonic object detection device including at least two independent transducers capable of emitting at least two ultrasonic signals, respectively, to produce as feedback reflected ultrasonic signals, and capable of receiving the reflected ultrasonic signals, comprising:
an electronic processing unit configured to:
convert the reflected ultrasonic signals received into corresponding spectrograms, within an audible frequency band, and
form corresponding audible time signals by inverse Fourier transform of the spectrograms,
wherein each of the least two independent transducers comprises a dual-frequency, triple-radiation-diagram, triaxial transducer comprising:
an annular metal resonator with central narrowing with a cylindrical shoulder, and
two annular-shaped piezoelectric ceramics arranged on either side of the metal resonator, one for causing a vibration of the cylindrical shoulder according to the axis of symmetry thereof, and the other for causing vibrations according to two axes that are mutually perpendicular and perpendicular to the axis of symmetry of the cylindrical shoulder.

2. The ultrasonic object detection device according to claim 1, wherein the electronic processing unit can be connected to an audio reproduction headset to reproduce the corresponding audible time signals.

3. The ultrasonic object detection device according to claim 1, wherein the electronic processing unit is furthermore capable of being connected to an external device capable of performing at least a portion of the processing performed on the signals.

4. The ultrasonic object detection device according to claim 1, further comprising an accelerometer, a magnetometer, and a gyroscope for associating an orientation in relation to vertical and magnetic north with the probed solid angle.

5. The ultrasonic object detection device according to claim 1, further comprising a capacitive sensor or an accelerometer for activating or putting on standby the object detection device.

6. A pair of glasses equipped with an ultrasonic object detection device according to claim 1.

7. A method for ultrasonic object detection including:
emitting at least two ultrasonic signals by at least two independent transducers, respectively, to produce reflected ultrasonic signals as feedback,
receiving the reflected ultrasonic signals by the at least two independent transducers,
converting the reflected ultrasonic signals into corresponding spectrograms, within an audible frequency band, and
forming corresponding audible time signals by inverse Fourier transform of the spectrograms,
wherein each of the at least two independent transducers comprises a dual-frequency. triple-radiation-diagram. triaxial transducer comprising an annular metal resonator with central narrowing with a cylindrical shoulder, and two annular-shaped piezoelectric ceramics arranged on either side of the metal resonator, the method further comprising:
respectively using the two ceramics to cause a vibration of the cylindrical shoulder according to the axis of symmetry thereof and cause vibrations according to two axes that are mutually perpendicular and perpendicular to the axis of symmetry of the cylindrical shoulder.

8. The method of ultrasonic object detection according to claim 7, wherein the converting of the reflected ultrasonic signals into corresponding spectrograms includes a projection of values of digitized signals formed from the reflected ultrasonic signals over at least a portion of the audible frequency band.

9. The method of ultrasonic object detection according to claim 7, further comprising a step of amplifying the received ultrasonic signals with a gain proportional to the delay.

10. The method of ultrasonic object detection according to claim 7, further comprising a step of translating the spectrograms.

11. The method of ultrasonic object detection according to claim 7, further comprising a step of reproducing the audible signals in an audio headset configured to be worn by a user.

12. A non-transitory recording medium, readable by a computer, on which a computer program is recorded comprising instructions for executing the method according to claim 7.

* * * * *